US006461318B2

(12) United States Patent
Freeman et al.

(10) Patent No.: US 6,461,318 B2
(45) Date of Patent: Oct. 8, 2002

(54) ANATOMICAL BRACE WITH RAPID-RELEASE SECUREMENT MEMBERS

(76) Inventors: Brad Freeman, 26822 via Zaragosa, Mission Viejo, CA (US) 92691; Danny Castillo, 253 Cozumel Ct., Laguna Beach, CA (US) 92651; Ricardo Jimenez, 9757 Dakota Ave., Garden Grove, CA (US) 92844; Billy Frank, 4 Chaumont Cir., Foothill Ranch, CA (US) 92610; Dave Castillo, 26445 Bautista, Mission Viejo, CA (US) 92692; Mark Wilson, 26275 Pacato Dr., Mission Viejo, CA (US) 92691

( * ) Notice: Subject to any disclaimer, the term of this patent is extended or adjusted under 35 U.S.C. 154(b) by 66 days.

(21) Appl. No.: 09/771,763

(22) Filed: Jan. 29, 2001

(65) Prior Publication Data

US 2002/0103449 A1 Aug. 1, 2002

(51) Int. Cl.$^7$ .................................................. A61F 5/00
(52) U.S. Cl. ........................................... 602/23; 602/26
(58) Field of Search .............................. 602/5, 16, 23, 602/26, 27; 128/882

(56) References Cited

U.S. PATENT DOCUMENTS

| 1,390,915 A | 9/1921 | Loth |
| 2,531,486 A | 11/1950 | Weber |
| 2,883,982 A | 4/1959 | Rainey |
| 3,030,634 A | 4/1962 | Bair |
| 3,099,448 A | 7/1963 | Salvo et al. |
| 3,387,305 A | 6/1968 | Shafer |
| 3,669,105 A | 6/1972 | Castiglia |
| 3,779,654 A | 12/1973 | Horne |
| 3,785,372 A | 1/1974 | Craig |
| 3,817,244 A | 6/1974 | Taylor |
| 3,900,898 A | 8/1975 | Kerman |
| 3,902,482 A | 9/1975 | Taylor |
| 3,928,872 A | 12/1975 | Johnson |
| 3,958,569 A | 5/1976 | Vosburgh |
| 4,136,404 A | 1/1979 | Lange |
| 4,169,467 A | 10/1979 | Rabischong et al. |

(List continued on next page.)

FOREIGN PATENT DOCUMENTS

| DE | 1491569 | 7/1969 |
| DE | 2432766 | 3/1975 |
| EP | 297766 A | 4/1989 |
| WO | 8404240 | 11/1984 |

*Primary Examiner*—Michael A. Brown
(74) *Attorney, Agent, or Firm*—Stetina Brunda Garred & Brucker

(57) ABSTRACT

An exteriorly positionable anatomical brace for protecting a uniting pivoting joint disposed between a first limb structure and a second limb structure of a living being. The brace includes a first cuff partially encompassable about the first limb structure and a second cuff partially encompassable about the second limb structure with each cuff being a generally U-shape structure with two lateral arms. A respective quick-release cuff retainer secures each cuff on each limb, and includes opposing first and second limb wraps for positioning around the limb. At least one limb wrap has a proximal portion provided with at least one externally accessible releasable connector for attaching the limb wrap to the respective lateral arm, while both limb wraps have distal portions interfacedly connected with each other with a tightenable interfacing retainer member. A pivotable brace joint member connects the first and second cuffs and is situated adjacent the pivoting joint to be stabilized.

10 Claims, 2 Drawing Sheets

U.S. PATENT DOCUMENTS

| | | |
|---|---|---|
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Ericksen et al. |
| D269,379 S | 6/1983 | Bledsoe |
| 4,407,276 A | 10/1983 | Bledsoe |
| 4,428,369 A | 1/1984 | Peckham et al. |
| 4,487,200 A | 12/1984 | Feanny et al. |
| 4,489,718 A | 12/1984 | Martin |
| 4,493,316 A | 1/1985 | Reed et al. |
| 4,494,534 A | 1/1985 | Hutson |
| 4,503,846 A | 3/1985 | Martin |
| 4,523,585 A | 6/1985 | Lamb et al. |
| 4,554,913 A | 11/1985 | Womack et al. |
| 4,559,998 A | 12/1985 | Castillo |
| D284,702 S | 7/1986 | Castillo |
| 4,603,690 A | 8/1986 | Skeen |
| 4,614,181 A | 9/1986 | Karlsson |
| 4,620,532 A | 11/1986 | Houswerth |
| 4,621,624 A | 11/1986 | Rayboy |
| 4,628,916 A | 12/1986 | Lerman et al. |
| 4,665,905 A | 5/1987 | Brown |
| 4,681,097 A | 7/1987 | Pansier |
| 4,697,583 A | 10/1987 | Mason et al. |
| 4,699,129 A | 10/1987 | Aaserude et al. |
| 4,715,363 A | 12/1987 | Detty |
| 4,723,539 A | 2/1988 | Townsend |
| 4,753,240 A | 6/1988 | Sparks |
| D298,568 S | 11/1988 | Womack |
| 4,791,916 A | 12/1988 | Paez |
| 4,803,975 A | 2/1989 | Meyers |
| 4,854,308 A | 8/1989 | Drillio |
| 4,856,501 A | 8/1989 | Castillo et al. |
| 4,886,054 A | 12/1989 | Castillo et al. |
| 4,938,207 A | 7/1990 | Vargo |
| 4,940,044 A | 7/1990 | Castillo |
| 4,964,402 A | 10/1990 | Grim et al. |
| 4,986,264 A | 1/1991 | Miller |
| D318,736 S | 7/1991 | Castillo |
| 5,063,916 A | 11/1991 | France et al. |
| 5,121,742 A | 6/1992 | Engen |
| 5,135,469 A | 8/1992 | Castillo |
| 5,230,697 A | 7/1993 | Castillo et al. |
| 5,288,287 A | 2/1994 | Castillo |
| D346,028 S | 4/1994 | Lengyel |
| D357,070 S | 4/1995 | Castillo |

ANATOMICAL BRACE WITH RAPID-RELEASE SECUREMENT MEMBERS

CROSS REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

This invention relates in general to braces for human joint support, and in particular to an exteriorly positionable anatomical brace having cuffs situated about respective limb structures on either side of a uniting pivoting joint such as a knee joint where each cuff is retained in place by cuff retainers having externally accessible and quickly engageable and releasable connectors.

Both injury and disease can affect the health, well-being, and operability of various joints of the human body. Chief among such joints are the knee and elbow where disease such as osteo-arthritis can curtail normal activity or where an injury such as a sports-related abuse or impact can prevent or severely limit continued activity. One manner of protecting joints is to fit the wearer with an appropriate brace whereby a pivotal support member is positioned adjacent the affected joint and held in place usually by cuff members situated around limb structure sites above and below the supported joint. As is apparent, the cuff members are responsible for stabilizing the support member and therefore must be well secured to their associated limbs.

To accomplish such securement, present cuff members are typically provided with one or more straps that are tightened around each limb structure and retained by buckles, hook-and-loop connections, or the like. Each time a user places or removes the brace, such user must reach for, locate, and manipulate the retention straps in an effort to either properly tighten the cuff members or to remove them. When a brace is in place in association with the supported joint, the retention straps many times are situated in a difficult-to-reach location which many times is behind the cuff members. Such placement means that the user is subjected at best to difficult donning and removal of the brace, and at worst to an improperly placed retention strap which interferes with brace usefulness.

In view of these drawbacks, it is apparent that a need is present for an easily, and therefore effectively, positionable brace. Accordingly, a primary object of the present invention is to provide an exteriorly positionable anatomical brace having readily accessible quick connect and disconnect retention members that inherently position and maintain retention members advantageously.

Another object of the present invention is to provide such a brace wherein required retention member tightness, once established, is replicated each time the brace is placed.

Yet another object of the present invention is to provide such a brace wherein a resilient liner is disposed against interior walls of the brace for user comfort.

These and other objects of the present invention will become apparent throughout the description thereof which now follows.

BRIEF SUMMARY OF THE INVENTION

The present invention is an exteriorly positionable anatomical brace for protecting a uniting pivoting joint disposed between a first limb structure and a second limb structure of a living being. The brace comprises a first cuff partially encompassable about the first limb structure and a second cuff partially encompassable about the second limb structure with each cuff being a generally U-shape structure with two lateral arms for juxtapositioning with respective adjacent limb structure sites. A respective cuff retainer secures each cuff on each respective limb, and comprises opposing first and second limb wraps extending toward each other from each respective lateral arm for positioning around the limb. At least one of the two opposing limb wraps has a proximal portion provided with at least one externally accessible releasable connector for attaching the limb wrap to the respective lateral arm, and each limb wrap has a distal portion. These distal portions of the first and second wraps are interfacedly connected with each other with a tightenable interfacing retainer member. Finally, a pivotable brace joint member connects the first and second cuffs and is situated adjacent the pivoting joint to be protected. In this manner the maintenance of brace placement and effectiveness is achieved by providing cuff retainers that are connectable and disconnectable from the encompassing cuff without requiring assembly and disassembly of the cuff retainers themselves.

BRIEF DESCRIPTION OF THE DRAWINGS

An illustrative and presently preferred embodiment of the invention is shown in the accompanying drawings in which.

DETAILED DESCRIPTION OF THE PREFERRED EMBODIMENT

Figure 1:
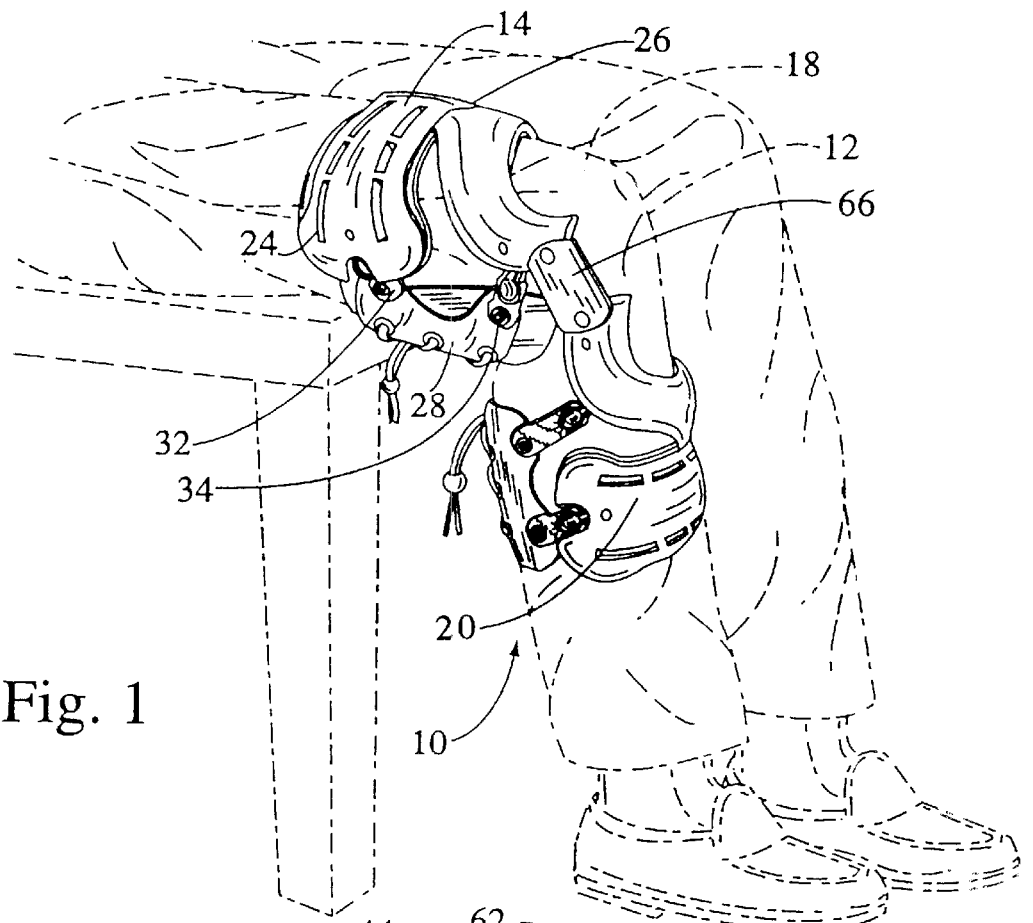
FIG. 1 is a side perspective view of an exteriorly positionable knee brace with cuffs in place on a leg.

Referring to the drawing figures, an exteriorly positionable anatomical brace 10 is shown in place on a leg 12 of a human being. The brace 10 has a first cuff 14 encompassed about the limb structure above the knee joint 18 and a second cuff 20 encompassed about the limb structure below the knee joint 18. Each cuff 14, 20 is a generally U-shape structure, which non-limitedly can be fabricated of a polymer plastic, for juxtapositioning with respective adjacent limb structure sites. While FIGS. 2 and 3 show only the upper cuff 14, it is to be understood that the following description thereof regarding limb wraps defined below applies equally to the lower cuff 20.

Figure 2:
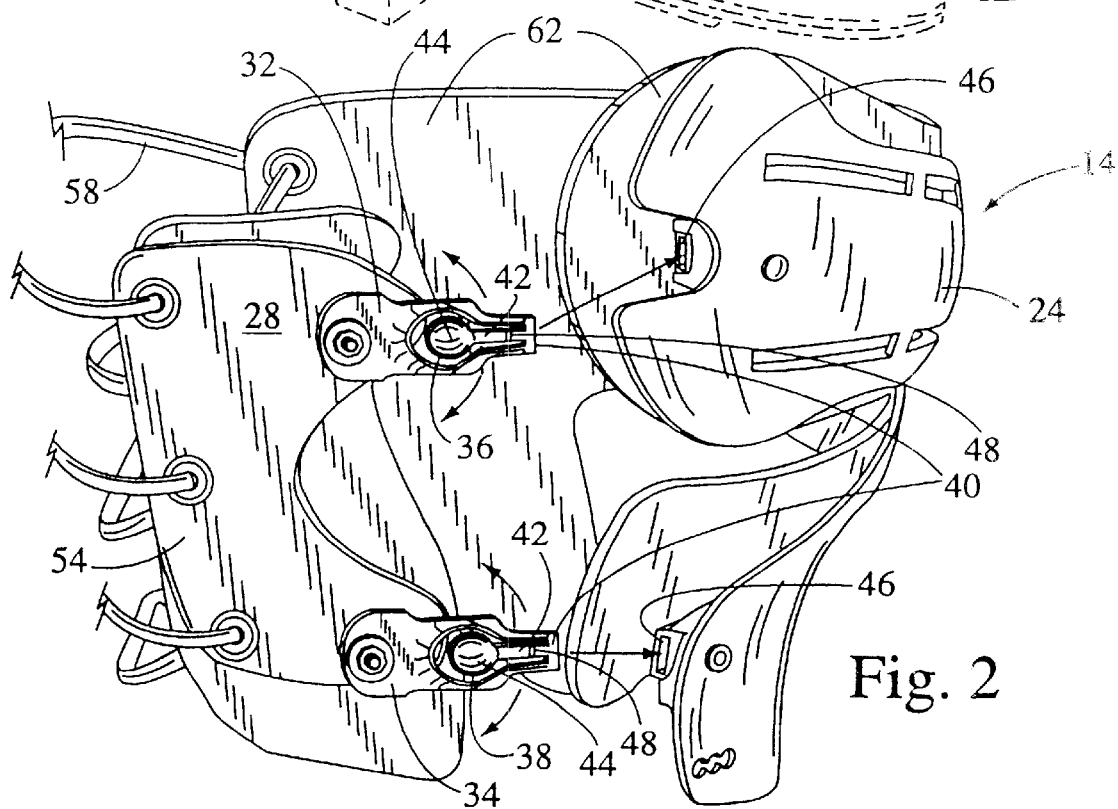
FIG. 2 is a side perspective view of the upper cuff and limb wrap of the brace of FIG. 1 in disassociated relationship.
Figure 3:
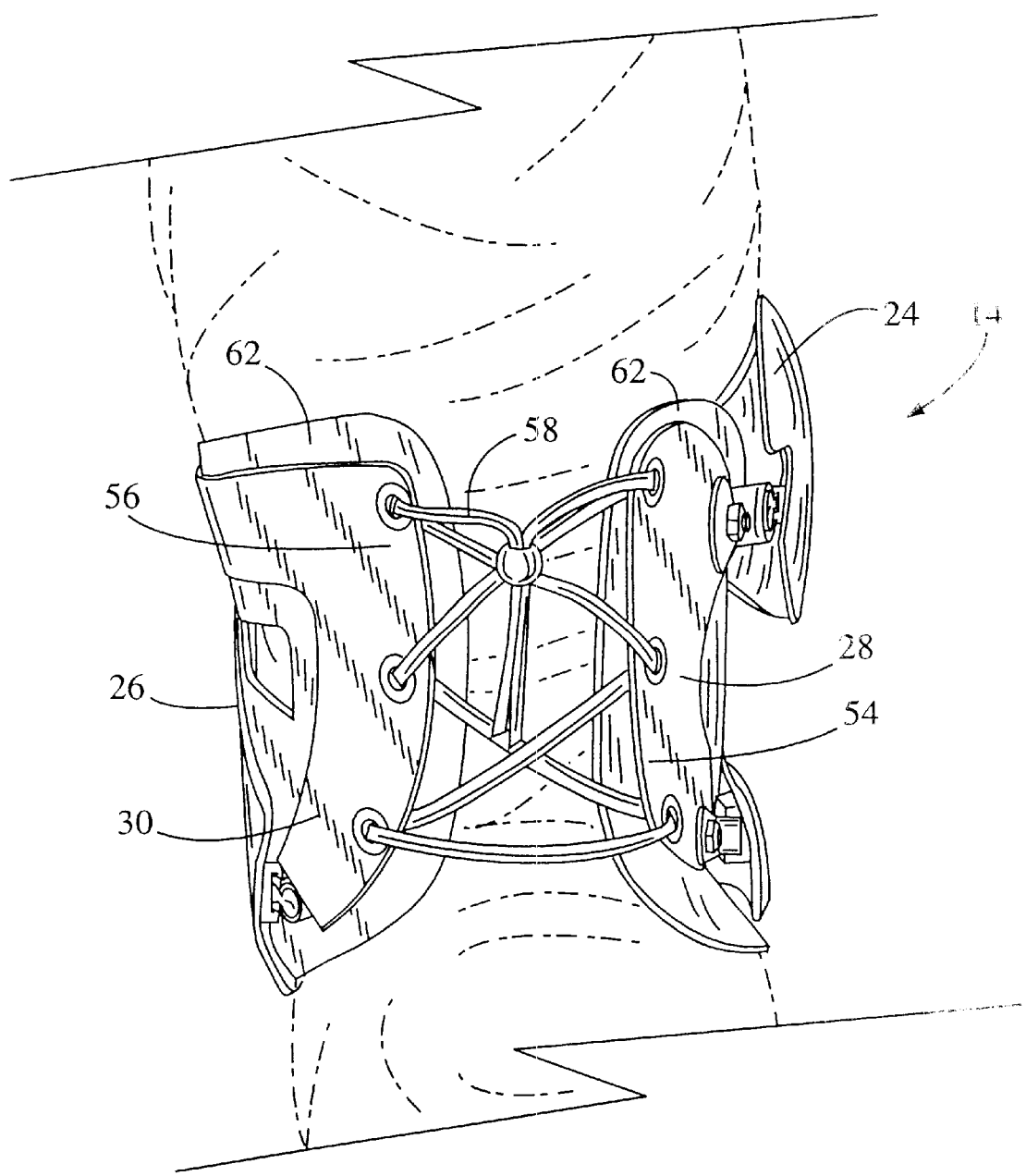
FIG. 3 is a rear perspective view of the upper cuff and limb wrap of FIG. 2 in place on a leg.

Thus, as shown in FIGS. 2 and 3, the cuff 14 has lateral arms 24, 26, with each arm 24, 26 having respectively attached thereto respective first and second limb wraps 28, 30 generally extendable toward each other from each lateral arm 24, 26 for positioning around the limb and functioning collectively as a cuff retainer. Each limb wrap 28, 30 is preferably constructed of a sewn fabric as known in the art and is attached proximally to the respective arms 24, 26. At least one limb wrap 28 is so attached by two releasable connectors 32, 34 having finger-operable releases 36, 38 for disengaging the limb wrap 28 from the corresponding lateral arm 24. As especially shown in FIG. 2, preferred connectors 32, 34 each comprise a tab member 40 with an outwardly spring-biased wall 42 with a finger-accessible extension 44, and a slot 46. While the slots 46 here shown are disposed on the cuff 14 and the tab members 40 are disposed on the limb wraps 28, 30, it is, of course, to be understood that such tab member and slot placement can be reversed. In operation, each tab member 40 is inserted into a respective receiving slot 46 where a hook 48 of its spring-biased wall 42 engages and is retained by a notch (not shown) in the adjacent wall 52 of the slot 46. Disengagement of the tab member 40 is accomplished by inwardly-directed finger pressure on the extension 44 which causes disengagement of the hook 48 from the notch and withdrawal of tab member 40.

Distal portions 54, 56 of the wraps 28, 30 are interfacedly connected with each other, when the brace 10 is in place on a user, by a tightenable interfacing retainer member here non-limitedly exemplified as a length of lace 58 intertwined through a plurality of eyelets 60 disposed through the distal portions 54, 56 of the wraps 28, 30 in substantially the same manner as a shoe is laced. The interior surfaces of the cuffs 14, 20 and limb wraps 28, 30 preferably are provided with a resilient liner 62 such as a soft rubber which can be attached with hook and loop connection to thereby permit easy removal and replacement as necessary. A pivotable brace joint member 66 connects the first and second cuffs 14, 20 for placement adjacent the joint to be protected.

In operation, the brace 10 is placed at the limb site of a user and the cuffs 14, 20 with limb wraps 28, 30 attached are positioned about the involved limb structures. Upon first placement of the brace 10, the laces 58 are then tightened to appropriate tightness such that the cuffs 14, 20 are properly maintained and protection is provided for the limb-connecting joint. Once such lacing is accomplished the first time, relacing is not required during brace use. Specifically, when the user wishes to remove the brace, the user simply presses inwardly on the extensions 44 of the tab members 40 along the cuff 14 and the limb wrap 28 separates from the cuff 14 for easy brace removal. Subsequent re-positioning of the brace 10 merely requires placement thereof as previously situated on the limbs and re-connection of the earlier disengaged tab members 40 into respective slots 46. This re-connection requires no contact with, or re-adjustment of, the laces 58, and thereby assures proper brace placement without awkward and very possibly incorrect orientation of brace retention members.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. An exteriorly positionable anatomical brace for protecting a uniting pivoting joint disposed between a first limb structure and a second limb structure of a living being, the brace comprising:
    a) a first cuff partially encompassable about the first limb structure and a second cuff partially encompassable about the second limb structure, wherein each said cuff is a generally U-shape structure with two lateral arms for juxtapositioning with respective adjacent limb structure sites;
    b) a respective cuff retainer for securing each cuff on each respective limb, each said retainer comprising opposing first and second limb wraps extending toward each other from each respective lateral arm for positioning around the limb, with at least one said limb wrap having a proximal portion provided with at least one externally accessible releasable connector for attaching the limb wrap to the respective lateral arm and with each limb wrap having a distal portion, whereby distal portions of said first and second wraps are interfacedly connected with each other with a tightenable interfacing retainer member; and
    c) a pivotable brace joint member connecting the first and second cuffs.

2. An exteriorly positionable anatomical brace as claimed in claim 1 wherein the limb wraps are constructed of a sewn fabric.

3. An exteriorly positionable anatomical brace as claimed in claim 1 wherein the releasable connector comprises cooperating male and female connector members with a finger-operable release for disengaging said connector members.

4. An exteriorly positionable anatomical brace as claimed in claim 3 wherein the male and female connector members are a tab and a slot, wherein the tab member has an outwardly spring biased side wall for retaining said tab within the slot and an outwardly finger-accessible extension of said side wall for moving said side wall inwardly and releasing the tab from the slot.

5. An exteriorly positionable anatomical brace as claimed in claim 1 wherein the distal portions of the first and second wraps have a plurality of respective opposing eyelets therethrough and wherein the interfacing retainer member comprises a length of lace intertwined through said eyelets and having ends thereof releasably attachable to each other.

6. An exteriorly positionable anatomical brace for protecting a uniting pivoting joint disposed between a first limb structure and a second limb structure of a living being, the brace comprising:
    a) a first cuff partially encompassable about the first limb structure and a second cuff partially encompassable about the second limb structure, wherein each said cuff is a generally U-shape structure with two lateral arms for juxtapositioning with respective adjacent limb structure sites;
    b) a respective cuff retainer for securing each cuff on each respective limb, each said retainer comprising opposing first and second limb wraps extending toward each other from each respective lateral arm for positioning around the limb, with at least one said limb wrap having a proximal portion provided with at least one externally accessible releasable connector for attaching the limb wrap to the respective lateral arm and with each limb wrap having a distal portion, whereby distal portions of said first and second wraps are interfacedly connected with each other with a tightenable interfacing retainer member;
    c) a resilient liner disposed against interior walls of each cuff and each cuff retainer; and
    d) a pivotable brace joint member connecting the first and second cuffs.

7. An exteriorly positionable anatomical brace as claimed in claim 6 wherein the limb wraps are constructed of a sewn fabric.

8. An exteriorly positionable anatomical brace as claimed in claim 6 wherein the releasable connector comprises cooperating male and female connector members with a finger-operable release for disengaging said connector members.

9. An exteriorly positionable anatomical brace as claimed in claim 8 wherein the male and female connector members are a tab and a slot, wherein the tab member has an outwardly spring biased side wall for retaining said tab within the slot and an outwardly finger-accessible extension of said side wall for moving said side wall inwardly and releasing the tab from the slot.

10. An exteriorly positionable anatomical brace as claimed in claim 6 wherein the distal portions of the first and second wraps have a plurality of respective opposing eyelets therethrough and wherein the interfacing retainer member comprises a length of lace intertwined through said eyelets and having ends thereof releasably attachable to each other.

* * * * *